(12) United States Patent
Silva et al.

(10) Patent No.: US 7,608,724 B2
(45) Date of Patent: Oct. 27, 2009

(54) ANTIBACTERIAL AND/OR ANTIPROTOZOAL NITROMIDAZOLE DERIVATIVE COMPOUNDS WITH UREASE INHIBITOR ACTIVITY, PROCESS FOR PREPARING THESE COMPOUNDS AND USE IN PHARMACEUTICAL COMPOSITIONS AND MEDICINES

(75) Inventors: Antônio Silva, Araraquara (BR); Andressa Munhoz, Araraquara (BR); Jean Santos, Araraquara (BR); Rodolfo Camargo, Araraquara (BR); Lúcia Castro, Araraquara (BR); Renato Menegon, Araraquara (BR); Wagner Vilegas, Araraquara (BR); Antonio Ferreira, São Carlos (BR); Eliana Varanda, Araraquara (BR); Man Chin Chung, Araraquara (BR)

(73) Assignee: EMS S.A., Hortolandia, SP (BR)

( * ) Notice: Subject to any disclaimer, the term of this patent is extended or adjusted under 35 U.S.C. 154(b) by 83 days.

(21) Appl. No.: 10/577,331

(22) PCT Filed: Oct. 27, 2004

(86) PCT No.: PCT/BR2004/000210

§ 371 (c)(1),
(2), (4) Date: Jul. 31, 2006

(87) PCT Pub. No.: WO2005/041853

PCT Pub. Date: May 12, 2005

(65) Prior Publication Data
US 2007/0072929 A1    Mar. 29, 2007

(30) Foreign Application Priority Data
Oct. 28, 2003  (BR)  .................................... 0304761
Oct. 20, 2004  (BR)  .................................... 0404851

(51) Int. Cl.
*C07D 233/28* (2006.01)
*A01N 43/50* (2006.01)

(52) U.S. Cl. .................................. 548/327.5; 514/392
(58) Field of Classification Search .............. 548/327.5; 514/392
See application file for complete search history.

(56) References Cited

U.S. PATENT DOCUMENTS

| 4,160,827 A | 7/1979 | Cho et al. |
| 4,456,610 A | 6/1984 | Hofheinz et al. |
| 4,482,722 A | 11/1984 | Thorbek et al. |
| 6,271,250 B1 * | 8/2001 | Yu .............................. 514/397 |
| 6,423,707 B1 | 7/2002 | Yang et al. |

FOREIGN PATENT DOCUMENTS

| CN | 1390836 A | 1/2003 |
| CN | 1400312 A | 3/2003 |
| EP | 330 201 A2 | 8/1989 |
| GB | 1 355 529 A | 6/1974 |
| GB | 1453417 A | 10/1976 |

OTHER PUBLICATIONS

Permentier et al. (CAPLUS abstract, Accession # 1993:81376, Bulletin des Societes Chimiques Belges (1992), 101(8), 701-7).*
Vermeersch et al. (CAPLUS Abstract, accession # 1990:526092, International Journal of Pharmaceutics (1990), 60(3), 253-60).*
Bundgaard (Design of Prodrugs, (1985), Elsevier, pages included 1-28).*
Krogsgaard-Larsen et al. (Textbook of Drug Design and Discovery, (2002), pages included: 428, 456, 457).*
Amtul et al. (Current Medicinal Chemistry, 2002, vol. 9, No. 14, p. 1323-48).*
Beaman et al., Antimicrobial Agents and Chemotherapy, Vol Date 1967, 1968, pp. 520-530.
Skupin et al., Tetrahedron: Asymmetry, vol. 8, No. 14, 1997, pp. 2453-2464.
Borlinghaus et al., Cancer Research, vol. 47, No. 15, 1987, pp. 4071-4075.
Tian et al., Chinese Journal of Chemistry, vol. 21, No. 7, 2003, pp. 853-857.
Webb et al., Journal of Laelled Compounds and Radiopharmaceuticals, vol. 28, No. 3, 1990, pp. 265-271.
Pfoertner et al., Journal Helvetical Chimica Acta, vol. 70, No. 1, 1987, pp. 171-174.
Woo et al., Arch Pharm Res., vol. 21., No. 1, pp. 6-11, (Feb. 1998). (abstract).
Ito et al., Eur J Phamacol., vol. 345, No. 2, pp. 193-198, (Mar. 19, 1998). (abstract).
Menendez et al., Mutat Res., vol. 478, No. 1-2, pp. 153-158, (Jul. 1, 2001). (abstract).
Cho et al., J Pharm Sci., vol. 8, No. 8, pp. 883-885, (Aug. 1985). (abstract).
Mahfouz et al., J Pharm Pharmacol., vol. 53, No. 6, pp. 841-848, (Jun. 2001). (abstract).
Park et al., Biol Pharm Bull, vol. 19, No. 2, pp. 182-187, (Feb. 1996). (abstract).
Ohta et al., Biochem Biophys Res Commun., vol. 285, No. 3, pp. 728-733, (Jul. 20, 2001). (abstract).

(Continued)

*Primary Examiner*—Rebecca L Anderson
*Assistant Examiner*—Robert Havlin
(74) *Attorney, Agent, or Firm*—Birch, Stewart, Kolasch & Birch, LLP

(57) ABSTRACT

The present application describes nitroimidazolic derivative compounds with antibacterial and/or antiprotozoal activity, which are potent urease inhibitors. It also describes the process for preparing those compounds and their use in pharmaceutical compositions and medicines.

11 Claims, 1 Drawing Sheet

OTHER PUBLICATIONS

Figure 1:
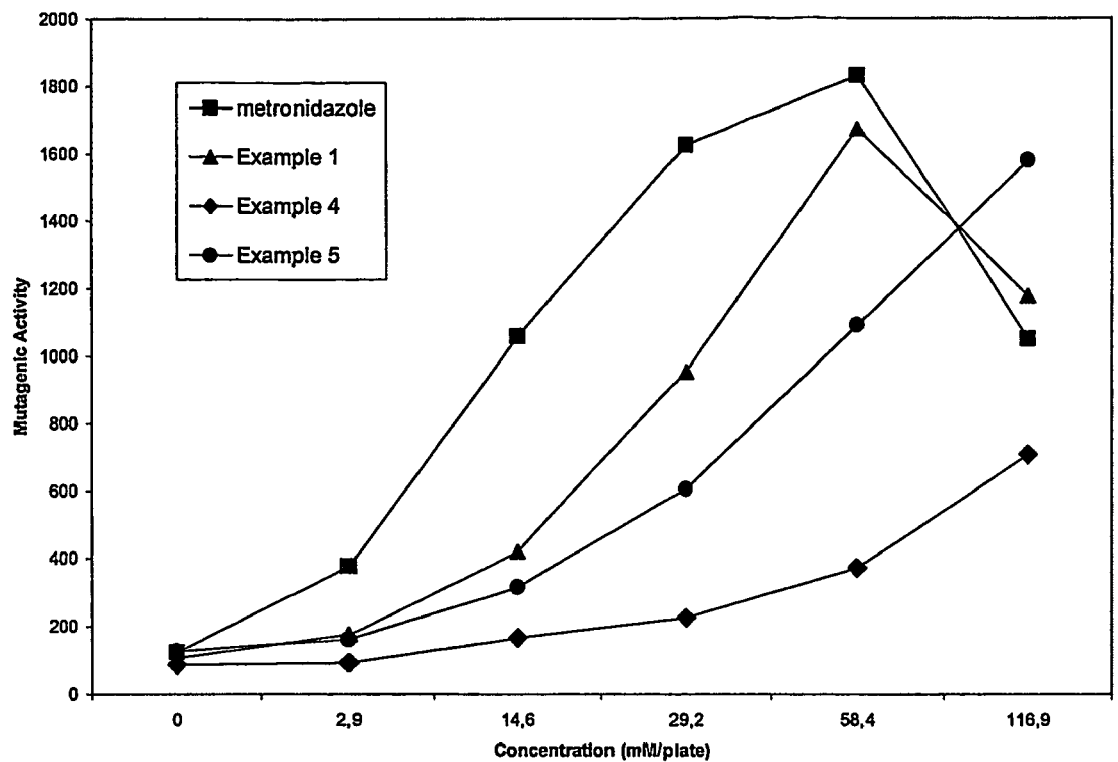

Odake et al., Biol Pharm Bull. vol. 17, No. 10, pp. 1329-1332, (Oct. 1994). (abstract).

Kuhler et al., J Med Chem., vol. 38, No. 25, pp. 4906-4916, (Dec. 8, 1995). (abstract).

Nagata et al., Antimicrobial Agents and Chemotherapy, vol. 39, No. 10, pp. 2187-2192, (Oct. 1995).

Houimel et al., Eur. J. Biochem., vol. 262, pp. 774-780, (1999).

Chung et al., Brazilian Journal of Pharmaceutical Sciences, vol. 41, No. 2, pp. 155-178, (Jun. 2005). Abstract (see p. 174).

* cited by examiner

ANTIBACTERIAL AND/OR ANTIPROTOZOAL NITROMIDAZOLE DERIVATIVE COMPOUNDS WITH UREASE INHIBITOR ACTIVITY, PROCESS FOR PREPARING THESE COMPOUNDS AND USE IN PHARMACEUTICAL COMPOSITIONS AND MEDICINES

This application is a National Stage entry of international application PCT/BR2004/000210, filed on Oct. 27, 2004, for which priority is claimed under 35 U.S.C. § 120, and this application claims priority to Brazilian Applications P10404851-2, filed on Oct. 20, 2004 and P10304761-0, filed on Oct. 28, 2003 under 35 U.S.C. § 119.

The present application describes nitroimidazolic derivative compounds with antibacterial and/or antiprotozoal activity, which are potent urease inhibitors. It also describes the process for preparing those compounds and their use in pharmaceutical compositions and medicines.

For the last 25 years, an alarming number of bacterial strains had developed resistance to several antimicrobial agents. Pathologies, as pharyngitis and laryngitis, that could be easily controlled and cured by using reduced dosages of antibacterial agents, nowadays are very difficult to treat. The major problem resides in the determination of microorganisms that are resistant to antimicrobial agents, because those microorganisms can undergo spontaneous mutation against any agent present in their environment once every $10^5$ to $10^{10}$ cell divisions. So, in the face of this elevate multiplication rate, a mutant can rapidly multiply itself in the presence of the antimicrobial agent producing a new population of resistant microorganisms.

Several issues lead to antimicrobial drugs resistance, for instance, their incorrect and indiscriminate utilization for treating flu and cold; their utilization by patients presenting difficulty in following the prescribed treatment and by self-medication; their utilization in prophylaxis after surgical procedures in immunodepressed patients and in long acne treatments; and by bacterial dissemination through distinct geographical regions. Bacterial resistance problem increases in developing countries, because in some countries it is possible to by potent antimicrobial agents in drugstores without prescription, witch facilitates the development of resistance.

Currently, one of the greatest challenges in biological research is to avoid that the treatment of infectious diseases can be compromised by the incredible ability that bacteria posses to develop resistance to every new antimicrobial agent produced.

The research field of the present invention is based in nitroimidazole derivative compounds belonging to imidazole class.

Nitroimidazoles are substances characterized by the presence of a pentagonal cyclic nucleus presenting two nitrogen atoms and a nitro group ($NO_2$) attached to it. The isolation of 2-nitroimidazole (also known as azomycin) from a *streptomyces* and the demonstration of its property against trichomonas stimulated the synthesis of this compound and the research of biological activities for other nitroimidazolic compounds, such as 2-(2-methyl-5-nitro-1H-imidazol-1-yl) ethanol also known as metronidazole.

Metronidazole is a broad spectrum nitromidazolic antimicrobial and was the first imidazole derivative introduced in human therapy. Metronidazole has an optimum clinic activity against several anaerobic and microaerobic pathogenic agents including Gram-positive and Gram-negative and it is classified as an antiprotozoal and antibacterial agent.

Metronidazole is an active compound against protozoans (*Balantidium coli*, *Blastocystis hominis*, *Chilomastix mesnili*, *Dracunculus medinensis*, *Entamoeba histolytica*, *Giardia lamblia* and *Trichomonas vaginalis*), Gram-negative bacteria (*Acidaminococcus* spp, *Bacteroides fragilis*, *Bacteroides distasonis*, *Bacteroides ovatus*, *Bacteroides thetaiotaomicron*, *Bacteroides vulgatus*, *Fusobacterium varium*, *Fusobacterium* spp., *Megasphaera*, *Veillonella parvula*, and *Veillonella* spp), Gram-positive bacteria (*Clostridium difficile*, *Clostridium perfringens*, *Clostridium ramosum*, *Clostridium* spp., *Eubacterium* spp., *Peptococcus* spp. and *Peptostreptococcus* spp), facultative anaerobic bacteria (*Gardnerella vaginalis* and *Helicobacter pylori*), *Campylobacter* spp and *Mycobacterium tuberculosis*.

Metronidazole activity against trichomonas was observed after its oral administration in patients with trichomoniasis and by the high healing behavior of this drug. Tests performed in patients with Vincent's stomatitis were also healed by drug activity of metronidazole.

However, biological research demonstrates the mutagenic activity of metronidazole and other imidazoles for bacteria and primitive eukaryotic systems. This activity was verified in *Salmonella typhimurium*, *Klebssiella pneumoniae*, *E. coli* and *Citrobacter freundii* tests.

Science teaches that mutation is every alteration of the genetic material from a cell that does not result in segregation or recombination. Mutation, when is not lethal to the cell itself, can propagate in a growing body (somatic mutation) or it can be transferred to new generations (germinal mutation) and it can be spontaneous or induced by physical, chemical or biological agents. It is already known that when mutation happens in somatic cells, it can lead to a carcinogenic process in the patient's organism. However, scientific research about carcinogenic effects of metronidazole still presents controversial results. Research demonstrates that metronidazole is carcinogenic to rodents, but considering tests in human beings, literature does not show conclusive results, requiring more experiments. If mutation takes place in germinative cells, it can lead to diseases and malformations in future generations.

Mutation and neoplasia represent abrupt alterations in a single cell, that are permanent and inherited by derivative cells. Thus, mutagenic tests are always recommended for the previous selection of chemical-pharmaceutical agents.

Nitro group ($NO_2$) is present in molecules from several active pharmaceutical ingredients, being directly attached to a benzene ring or as a part of heterocyclic rings. Nitro group is responsible for the antiparasitic activity of the compound and, as a consequence, it is indispensable in the molecule structure. However, scientific research demonstrates that the mutagenic activity of metronidazole and other 5-nitroimidazoles has a relationship with the presence of the nitro group ($NO_2$) and with the substitution on N-1 and/or N-3 (see metronidazole's chemical structure presented below). In this last case, mutagenic activity can be completely suppressed. Metronidazole mutagenic effect is improved by microssomal activation. The chemical structure of metronidazole is the following:

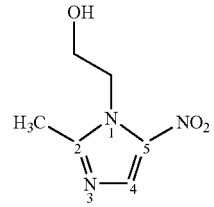

For this effect to happen, it is necessary an enzymatic reduction of the nitro group giving rise to mutagenic intermediate products, however, this process is not usual in mammalian cells. In human cells, metronidazole does not induce, in vitro or in vivo the changing of sister chromatids or micronucleus induction. Metronidazole clastogenic effect can be observed by the increase of chromosomal aberrations and by the induction of micronucleus in hamster ovarian cells (CHO) and in human lymphocytes. The ability of metronidazole and its metabolites in producing fractures in DNA of human cells has also being discussed. Studies from MENÉNDEZA et. al., DNA breakage due to metronidazole treatment, *Mutantion Research.*, 478, 153-158 (2001) concluded that therapeutic dosages of metronidazole produce damage to the DNA of circulating lymphocytes, that seamed to be repaired within 15 days after the end of the treatment, but there was a patient that the damage was not repaired. However, there is a lack of studies to determinate if DNA damages caused by metronidazole can promote the genesis of neoplasms.

New therapeutically chemical compounds are produced by latentiation of the parent drug, especially by esterification. Latentiation is an organic synthesis process that attempts to modify the molecule of a certain known drug or active molecule optimizing its pharmacokinetic properties and/or reducing its toxicity. Studies from Guido, R. V. C. et. Al, demonstrate a reduction of the mutagenic activity of compound NFOH-121 relatively to nitrofural (nitrofurazone), where the use of the technique enabled the lowering of mutagenic effect of the original active compound or parent drug (Revista Ciencia Farmaceutica; V.22, n° 2, 319-333 (2001)). In this research, the mutagenic effect of the nitro-compound was reduced by 300 to 400%, when comparing to the original active compound.

In the last years, latentiation has became one of the main tools for developing new chemotherapeutics for fighting major diseases like cancer and AIDS—Acquired Immunodeficiency Syndrome. Reasons that justify the search for new latent drugs are:

1—Pharmacokinetic inconveniences of the parent drug;
2—High toxicity of the parent drug;
3—Poor chemical stability of the parent drug;
4—Non appropriate water solubility of the parent drug;
5—Odor and taste inconveniences of the parent drug;
6—pharmaceutical formulation difficult to prepare with the parent drug.

Latent active compounds forms can also be used as prodrugs, like a compound that is chemically changed into an inactive unstable derivative by chemical and/or enzymatic reactions, which is converted to the parent drug inside the body, or after it reaches its action target. A pro-drug may be defined as any compound that suffers biotransformation before exhibiting its pharmacological effects. Even the prodrug as well as the analog present similar chemical structures, but their biological properties are different when considering: activity, potency, bioavailability, synthesis process, spectrum of activity, and therapeutic indices. The pro-drug and the analog differences themselves by the presence of an unstable chemical linkage (week and reversible) between the parent drug and the carrier group.

Among several methods for preparing pro-drugs, esterification is the most used, followed by amide, imide and carbamate formation. Currently, drugs functional groups can be modified by chemical reactions producing reversible groups largely used in pro-drugs development.

A great quantity of esters and hemiesters pro-drugs from metronidazol were synthesized for improving its hydrosolubility for parenteral administration, chemical stability, membrane cell permeation and to reduce enzymatic degradation susceptibility.

As disclosed before, metronidazole is a drug widely used in several bacterial and parasitic infections. Among infectious agents over it presents activity there is *Helicobacter pylori*.

*Helicobacter pylori* is the main cause of peptic ulcer being an etiologic agent that is related in the development of gastric cancer. It is believed that *H. pylori* infection reaches around 50% of the world population, and about 20% of people infected develop gastroduodenal disorders during their lifetime. This etiologic agent is responsible by peptic ulcer disease, primary gastritis, gastric mucosa-associated lymphoid-tissue lymphoma, and gastric adenocarcinoma As disclosed by Houimel M; Mach J; Corthèsy-Theulaz I; Corthèsy B; Fish I. New inhibitors of *Helicobacter pylori* urease holoenzyme selected from phage-displayed peptide libraries. Eur. J. Biochem; 202:774-780 p, 1998, several studies demonstrate the correlation between urease synthesis by *H. pylori* and its survival in the acidic environment of the stomach. This enzyme hydrolyzes urea and releases ammonia thus maintaining the periplasmic pH at 6,2. Urease-negative mutants were shown to be unable to colonize the gastric mucosa of animal species tested.

Currently therapy used to eradicate *Helicobacter pylori* is not totally efficient and requires a double, triple or quadruple therapy, which difficult the patients adherence to the therapy and increasing the probability of adverse and/or side effects and bacterial resistance. Normally therapy comprises in using one, two or three antibiotics associated to a proton pump inhibitor. Among usual compounds, for instance, proton pump inhibitors, omeprazole and rabeprazole are the only urease inhibitors used in the clinic, but they are not efficient in the eradication of this bacteria, and it is necessary to add at least one antimicrobial agent to the medicament composition.

Literature describes several nitroimidazolic derivative compounds used in the treatment of bacterial infections. However, there was not found any document describing nitroimidazolic derivative compounds that are also able to act as urease inhibitors.

The development of new compounds capable of inhibiting urease and also being compounds with antimicrobial and/or antiprotozoal activity, will allow an efficient and simplified treatment for infections caused by several pathogenic agents, in particular for treating infections caused by *H. pylori*, reducing the requirement for using complex therapies comprising the combination of several therapeutic agents. Those drugs would be even safer if they are designed or developed in order to present reduced mutagenic activity, inferior than observed in the parent drug (specially metronidazole).

It is possible to find in literature several references describing nitroimidazolic derivatives designed and developed for improving the characteristics of the prior drugs.

According to Cho & Haynes (CHO, M. J., HAYNES, L. C., Serum-catalyzed hydrolysis of metronidazole amino acid esters, *Journal of Pharmaceutical Science, V.* 74, n° 8, 883-885, 1985), the synthesis of metronidazole phosphate lead to an increase of metronidazole hydrosolubility by 50 times. Those researchers also esterified metronidazole with amino acids, which allowed the improvement of its solubility for parenteral usage with the plasmatic liberation of metronidazole and the amino acid.

The preparation of identical double esters has become an ordinary strategy for developing new pro-drugs, where two molecules of the parent drug are attached by means of a spacing compound. Mahfouz et. al. (MAHFOUZ, N. M., HASSAN, M. A., Synthesis, chemical and bioavailability in rabbits of metronidazole aminoacid ester prodrugs with enhanced water solubility *Journal of Pharmacy and Pharmacology,* 53, 841-848 (2001)) synthesized a series of double esters from metronidazole using different carboxylic acids (adipic, phtalic, glutaric, succinic and sebacic) as spacing agents. The study demonstrated that they were more lipophilic than the parent drug and stable enough in glucophysiological and in physiologic pH for being completely absorbed. The pro-drugs were converted to metronidazole with fast liberation of the first molecule and slow hydrolysis of the other. In vivo studies (mouse, rabbit) of these pro-drugs orally administered, demonstrated that they were absorbed in a non-ionized form, with an extended plasmatic release. Ternary esters of metronidazole were also tested with good results considering their hydrosolubility, chemical stability and metronidazole plasmatic release. However, none of these studies evaluated the compounds by means of their mutagenic activity, only concerning about the improvement of parent drug solubility and stability, without trying to improve the specificity and the activity of the parent drug.

Scientific literature shows that non-nitroimidazolic compounds, like hydroxamic and acetohydroxamic acids, hidroxyurea, thiourea, N,N'-dihydroxymethylurea, fluorofamide, omeprazole, acabet sodium and rabeprazole are urease inhibitors and they were tested in infections, mainly by *Helicobacter pylori*, as disclosed by SHIBATA K; HONGO A; KINOSHITA M. Ecabet sodium, a locally acting antiulcer drug, inhibits urease activity of *Helicobacter pylori*. Eur J Pharmacol; 345(2):193-8, 1998 Mar., KUHLER T C; FRYKLUND J; BERGMAN NA; WEILITZ J; LEE A; LARSSON H. Structure-activity relationship of omeprazole and analogues as *Helicobacter pylori* urease inhibitors. J Med Chem; 38(25):4906-16, 1995 Dec. 8, NAGATA K; TAKAGI E; SATOH H; OKAMURA H; TAMURA T. Growth inhibition of *Ureaplasma urealyticum* by the proton pump inhibitor lansoprazole: direct attribution to inhibition by lansoprazole of urease activity and urea-induced ATP synthesis in *U. urealyticum*. Antimicrob Agents Chemother; 39(10):2187-92, 1995 October, ODAKE S; MORIKAWA T; TSUCHIYA M; IMAMURA L; KOBASHI K. Inhibition of *Helicobacter pylori* urease activity by hydroxamic acid derivatives. Biol Pharm Bull; 17(10):1329-32, 1994 October, OHTA T; SHIBATA H; KAWAMORI T; IIMURO M; SUGIMURA T; WAKABAYASHI K. Marked reduction of *Helicobacter pylori*-induced gastritis by urease inhibitors, acetohydroxamic acid and flurofamide, in Mongolian gerbils. Biochem Biophys Res Commun; 285(3):728-33, 2001 Jul. 20, PARK J B; IMAMURA L; KOBASHI K. Kinetic studies of *Helicobacter pylori* urease inhibition by a novel proton pump inhibitor, rabeprazole. Biol Pharm Bull; 19(2):182-7, 1996 February, WOO T W; CHANG M S; CHUNG Y K; KIM KB; SOHN SK; KIM S G; CHOI W S. Inhibitory action of YJA20379, a new proton pump inhibitor on *Helicobacter pylori* growth and urease. Arch Pharm Res; 21(1):6-11, 1998 February.

U.S. Pat. No. 4,160,827 describes water soluble phosphate salts from metronidazole, that can be prepared as dosage forms where metronidazole is not possible to be used because it is insoluble. The examples describe the synthesis of several possible salts and dosage forms, but do not describe the effects over the activity, selectivity or toxicity of the proposed salts.

U.S. Pat. No. 4,456,610 describes 2-nitroimidazolic derivatives used in the treatment of filariasis. Those compounds present lower toxicity than the parent drug azomycin, demonstrating that the derivation of known compounds can lead to the development of safer compounds for therapeutic usage.

U.S. Pat. No. 4,482,722 describes a metronidazole ester derivative with N,N'-dimethylglycine and its addition salts. According to the authors, these compounds are water soluble and are specially useful for preparing parenteral pharmaceutical compositions suitable in the treatment of certain anaerobic infections. The ester hydrolysis rapidly in vivo releasing metronidazole into the organism. As the compound is a pro-drug from metronidazole, concern about mutagenic issue is relevant, once the parent drug is regenerated in vivo.

U.S. Pat. No. 6,423,707 discloses nitroimidazolic ester derivative compounds that are active against *Helicobacter pylori*, ratifying the efficiency of the latentiation process in the development of new compounds (pro-drugs) with antimicrobial activity. However, this patent does not mention nor suggest any urease inhibitor capacity of the disclosed esters, once the objective of the patent is directed only to improve antimicrobial activity of the esters described.

From the references disclosed before it is possible to notice that many nitroimidazolic derivatives were proposed searching for an improvement of the physical-chemical properties of the parent drugs, and in one specific case, lead to a compound less toxic than its antecessor, like the azomycin derivative used to treat filariasis.

As disclosed before, treatment of several infections with less toxic or mutagenic nitroimidazole derivatives possessing the ability of being multifunctional drugs acting over more than one target in the organism will be relevant in the treatment of several diseases.

The research developed by the applicant is related to the development of new antibacterial and/or antiparasitic nitroimidazole derivatives that are also active in inhibiting urease, a necessary enzyme used for the adaptation and the survival of several microorganisms in host organisms.

Consequently it is an objective of the present invention to improve the pharmacotherapy against a variety of aerobic and microaerobious pathogenic agents including protozoans, Gram-positive, Gram-negative and facultative anaerobic bacteria, preferably *Helicobacter pylori*, by using multifunctional compounds that, beside presenting antibacterial and or antiparasitic activity, are potent inhibitors of urease enzyme.

The advance reached by the present invention allows treating several diseases by using particularly the monotherapy, wherein the compounds of the present invention may be used in a safe way because they present reduced mutagenic activity when comparing to metronidazole, and because they are effective urease inhibitors, being particularly useful in the treatment of individuals infected by *Helicobacter pylori*.

Urease producing organisms, such as *Helicobacter pylori*, uses this enzyme for their defense and survival. These organisms promote the conversion of urea into ammonia, that neutralizes the hydrochloric acid from the gastric mucosa and stimulates the increase of the inflammatory process, with a possible progression to carcinoma.

According to the present invention, the described compounds act over the intruder microorganism, particularly *H. pylori*, in a selective and specific way. Due the low toxicity and/or mutagenicity of these compounds when comparing with metronidazole particularly, the therapeutic dosage to be used is safer, and there is no need to use therapeutic dosages near the toxic limit of these compounds.

Selectivity of the compounds of the present invention occurs by the presence of groups with affinity to urease, that direct the compound to the target (urease producing microorganisms), promoting within the target of action the antimicrobial activity by the presence of nitroimidazolic groups, besides inhibiting urease itself, which allows reverting the pH of the medium to an acidic pH that makes the survival of the pathogenic agent unfeasibly. Selectivity also happens by increasing the antimicrobial action when using an urease inhibitor. Action selectivity also promotes lowering toxicity, once the said compound will have preferential action over urease producing microorganisms, and it is not the situation of the intestinal mucosa cells. By this way, compounds developed in the present invention posses a higher selectivity by acting as double medicaments: exhibiting an antimicrobial effect and by inhibiting the survival mechanism of the microorganism in vivo.

Studies disclosed in the experimental part of this document like Ames Test or the test using *Salmonella typhimurium* for characterizing mutagenic activity clearly demonstrate an increase in the reliability for using the compounds of the present invention in human beings when comparing to the parent drug.

The present invention describes compounds of formula (I) and (II) represented below:

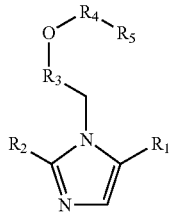

(I)

where
$R_1$=$NO_2$, $R_2$=$CH_3$ and $R_3$=$CH_2$, $CHCH_3$, $CHCH_2Cl$

OR, $R_1$=H, $R_2$=$NO_2$ and $R_3$=$O(CH_2)_4$, $OCH_2(CH)_2CH_2$, $OCH_2$—C≡C—$CH_2$, $CHCH_2OCH_3$, $CONH(CH_2)_{1-2}$,

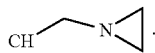

AND

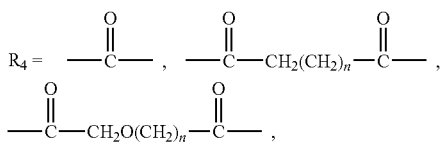

$CH_2CO$, where n=1-6

$R_5$=$NHCONH_2$, NHCONHOH, ONHCONHOH, $OCH_2NHCONHCH_2OH$, $NHCSNH_2$, NHCSNHOH, ONHCSNHOH, $OCH_2NHCSNHCH_2OH$, $NHCNHNH_2$, NHCNHNHOH, ONHCNHNHOH, $OCH_2NHCNHNHCH_2OH$

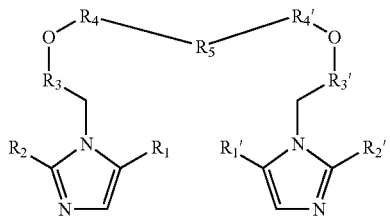

(II)

where
$R_1$ and $R_1'$=$NO_2$,
$R_2$ and $R_2'$=$CH_3$ and
$R_3$ and $R_3'$=$CH_2$, $CHCH_3$, $CHCH_2Cl$

OR $R_1$ and $R_1'$=H,
$R_2$ and $R_2'$=$NO_2$ and $R_3$ and $R_3'$=$O(CH_2)_4$, $OCH_2 (CH)_2CH_2$, $OCH_2$—C≡C—$CH_2$, $CHCH_2OCH_3$, $CONH(CH_2)_{1-2}$,

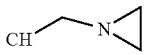

AND
$R_4$ and

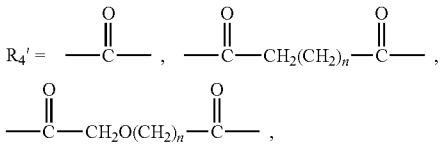

$CH_2CO$, where n=1-6

$R_5$ and $R_5'$=NHCONH, NHCONHO, ONHCONHO, $OCH_2NHCONHCH_2O$, NHCSNH, NHCSNHO, ONHCSNHO, $OCH_2NHCSNHCH_2O$, NHCNHNH, NHCNHNHO, ONHCNHNHO, $OCH_2NHCNHNHCH_2O$ The inventive compounds of formula (I) and (II) are useful in the treatment of infections caused by anaerobic, microaerobic microorganisms, including protozoans, Gram-positive, Gram-negative and facultative anaerobic bacteria. Compounds of formula (I) and (II) are particularly useful in the treatment of infections caused by urease producing organisms, specially *Helicobacter pylori*.

The present invention also comprises the addition pharmaceutical acceptable salts from compounds of general formulas (I) and (II), such as hydrochloride, hydrobromide, acetate, propionate, phosphate, sulfate, nitrate, maleate, fumarate, citrate, tartrate, methanesulfonate, besylate, among others, as also the hydrates.

Representative compounds of general formula (I) and (II) from the present invention include:

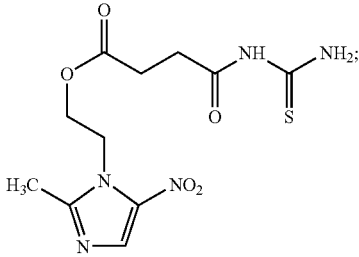

2-(2-methyl-5-nitro-1H-imidazol-1-yl) ethyl 4-[(aminocarbonothioyl) amino]-4-oxobutanoate

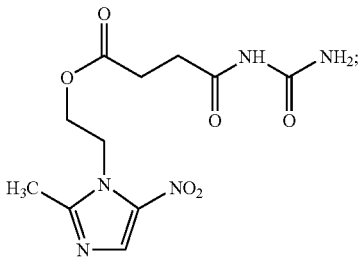

2-(2-methyl-5-nitro-1H-imidazol-1-yl) ethyl 4-[(aminocarbonyl) amino]-4-oxobutanoate

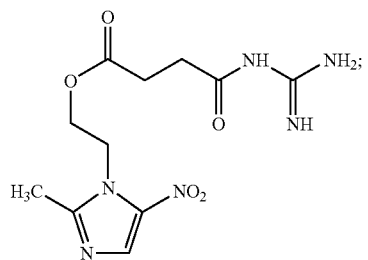

2-(2-methyl-5-nitro-1H-
imidazol-1-yl) ethyl 4-
{[amino (imino) methyl] amino}-
4-oxobutanoate

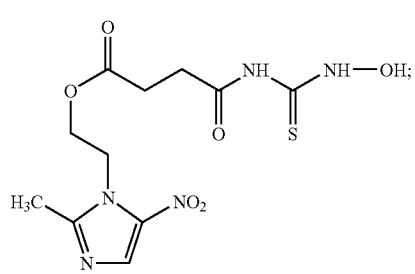

2-(2-methyl-5-nitro-1H-
imidazol-1-yl) ethyl 4-
{[(hydroxyamino) carbonothioyl]
amino}-4-oxobutanoate

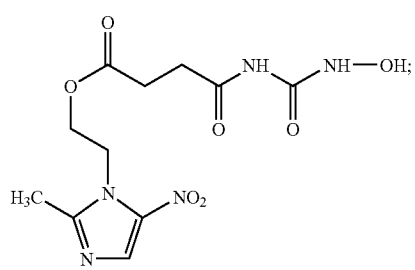

2-(2-methyl-5-nitro-1H-
imidazol-1-yl) ethyl 4-
{[(hydroxyamino) carbonyl] amino}-
4-oxobutanoate

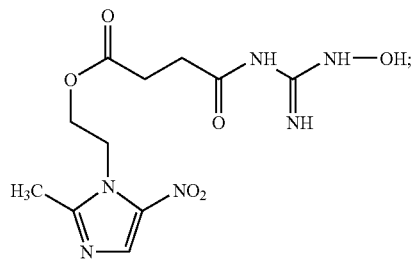

2-(2-methyl-5-nitro-1H-
imidazol-1-yl) ethyl 4-
{[(hydroxyamino) (imino) methyl]
amino}-4-oxobutanoate

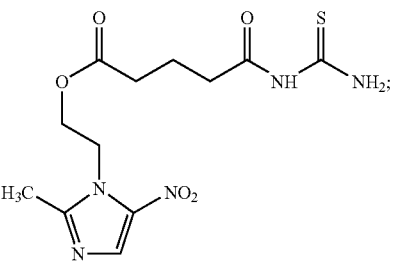

2-(2-methyl-5-nitro-1H-
imidazol-1-yl) ethyl 5-
[(aminocarbonothioyl) amino]-
5-oxopentanoate

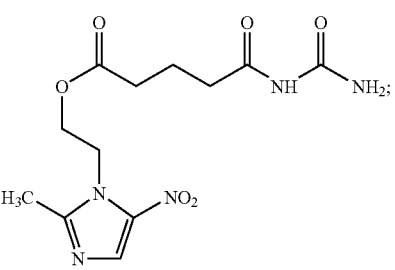

2-(2-methyl-5-nitro-1H-
imidazol-1-yl) ethyl 5-
[(aminocarbonyl) amino]-5-
oxopentanoate

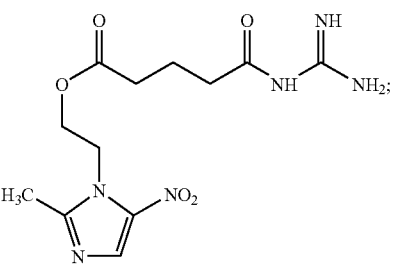

2-(2-methyl-5-nitro-1H-
imidazol-1-yl) ethyl 5-
{[amino (imino) methyl] amino}-
5-oxopentanoate

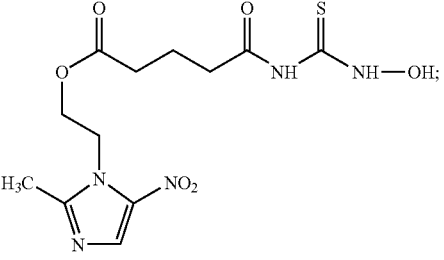

2-(2-methyl-5-nitro-1H-
imidazol-1-yl) ethyl 5-
{[(hydroxyamino) carbonothioyl]
amino}-5-oxopentanoate

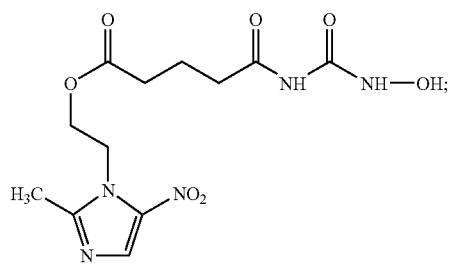

2-(2-methyl-5-nitro-1H-
imidazol-1-yl) ethyl 5-
{[(hydroxyamino)carbonyl]
amino}-5-xopentanoate

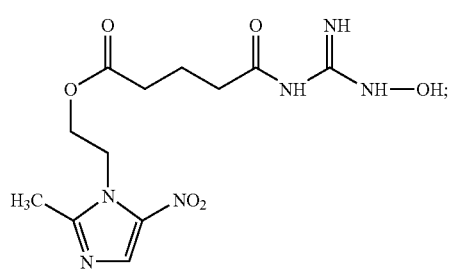

2-(2-methyl-5-nitro-1H-
imidazol-1-yl) ethyl 5-
{[(hydroxyamino) (imino) methyl]
amino}-5-oxopentanoate

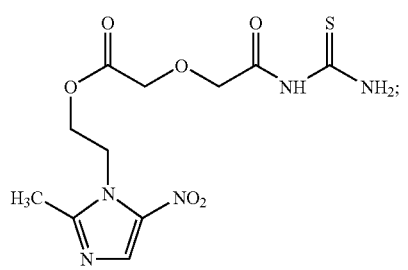

2-(2-methyl-5-nitro-1H-
imidazol-1-yl) ethyl {2-
[(aminocarbonothioyl) amino]-
2-oxoethoxy} acetate;

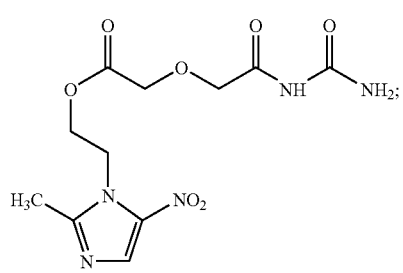

2-(2-methyl-5-nitro-1H-
imidazol-1-yl) ethyl {2-
[(aminocarbonyl) amino]-2-
oxoethoxy} acetate;

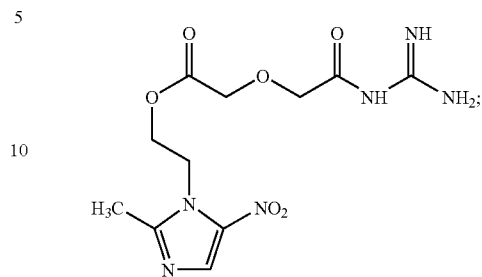

2-(2-methyl-5-nitro-1H-
imidazol-1-yl) ethyl (2-
{[(amino (imino) methyl] amino}-
2-oxoethoxy) acetate

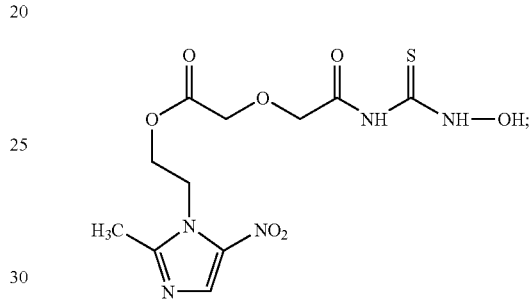

2-(2-methyl-5-nitro-1H-
imidazol-1-yl) ethyl (2-
{[(hydroxyamino) carbonothioyl]
amino}-2-oxoethoxy)acetate

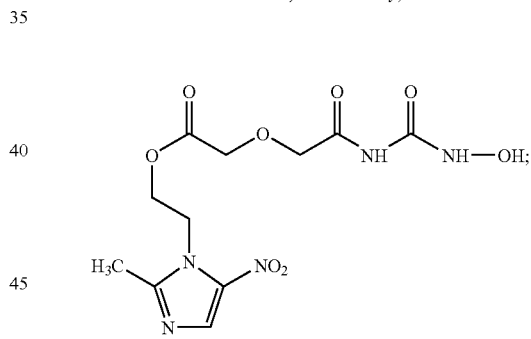

2-(2-methyl-5-nitro-1H-
imidazol-1-yl) ethyl (2-
{[(hydroxyamino) carbonyl] amino}-
2-oxoethoxy) acetate

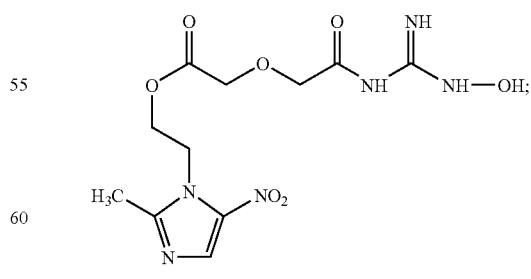

2-(2-methyl-5-nitro-1H-
imidazol-1-yl) ethyl (2-
{[(hydroxyamino) (imino)
methyl] amino}-2-oxoethoxy)
acetate -continued

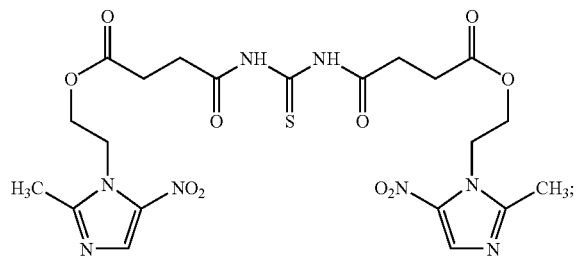

Bis[2-(2-methyl-5-nitro-1H-imidazol-1-yl) ethyl] 4,4′-[(thioxomethylene) diimino] bis (4-oxobutanoate)

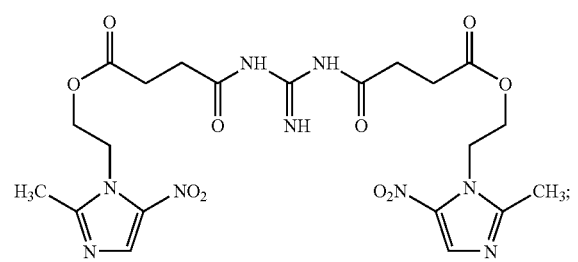

Bis[2-(2-methyl-5-nitro-1H-imidazol-1-yl) ethyl] 4,4′-[(iminomethylene) diimino] bis (4-oxobutanoate)

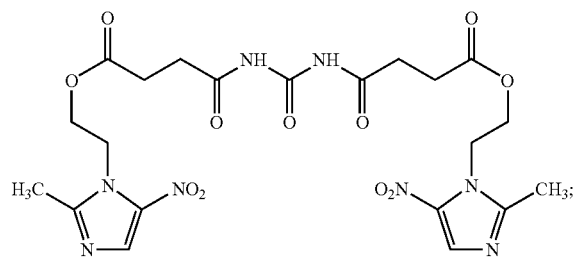

Bis[2-(2-methyl-5-nitro-1H-imidazol-1-yl) ethyl] 4,4′-(carbonyldiimino) bis (4-oxobutanoate)

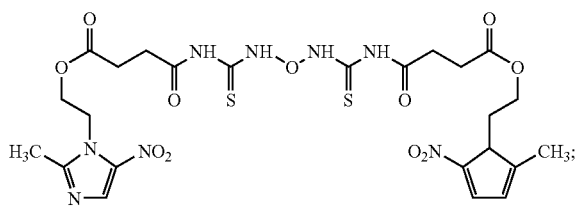

Bis[2-(2-methyl-5-nitro-1H-imidazol-1-yl) ethyl] 3,6, 2-trioxo-8,12-dithioxo-2,10-dioxa-7,9,11,13-tetraazaheptadecan-17-oate;

-continued

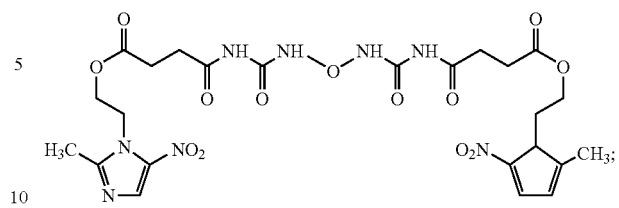

Bis[2-(2-methyl-5-nitro-1H-imidazol-1-yl) ethyl] 3,6,8,12,14-pentaoxo-2,10-dioxa-7,9,11,13-tetraazaheptadecan-17-oate;

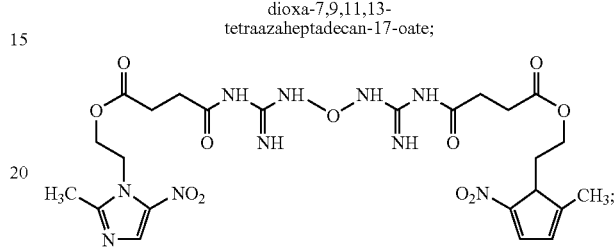

Bis[2-(2-methyl-5-nitro-1H-imidazol-1-yl) ethyl] 8,12-diimino-3,6,14-trioxo-2,10-dioxa-7,9,11,13-tetraazaheptadecan-17-oate;

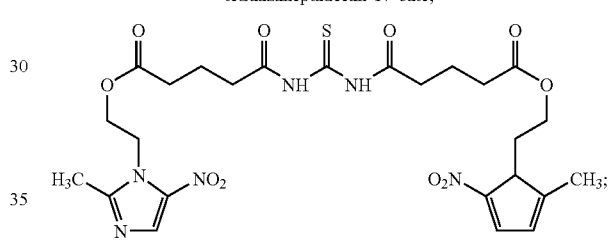

Bis[2-(2-methyl-5-nitro-1H-imidazol-1-yl)ethyl] 5,5′-[(thioxomethylene) diimino] bis (5-oxopentanoate);

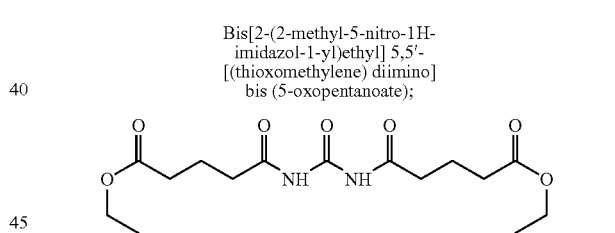

Bis[2-(2-methyl-5-nitro-1H-imidazol-1-yl) ethyl] 5,5′-(carbonyldiimino) bis (5-oxopentanoate);

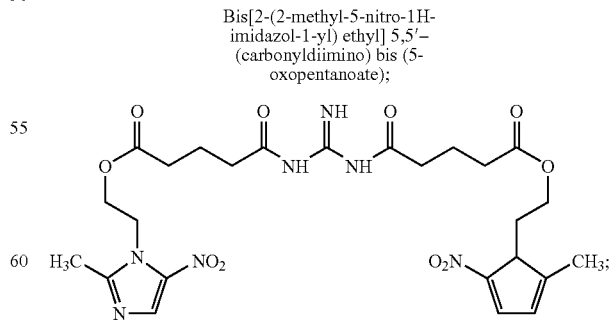

Bis[2-(2-methyl-5-nitro-1H-imidazol-1-yl) ethyl] 5,5′-[(iminomethylene) diimino]bis (5-oxopentanoate)

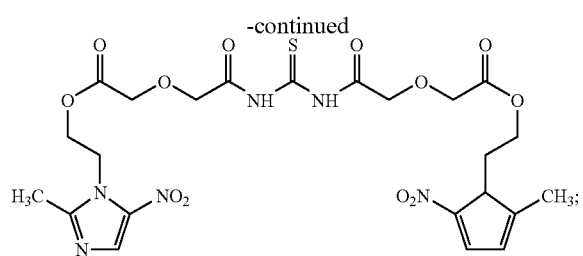

Bis[2-(2-methyl-5-nitro-1H-imidazol-1-yl) ethyl] 5,9-dioxo-7-thioxo-3,11-dioxa-6,8-diazatridecane-1,13-dioate

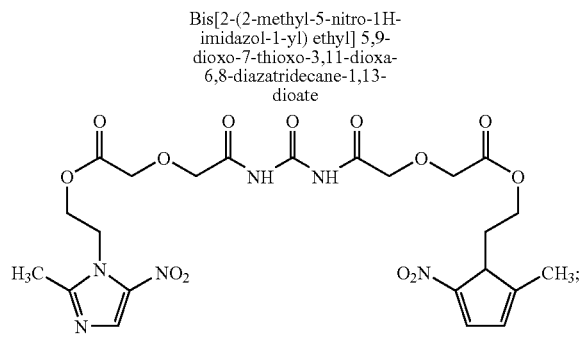

Bis[2-(2-methyl-5-nitro-1H-imidazol-1-yl) ethyl] 5,7,9-trioxo-3,11-dioxa-6,8-diazatridecane-1,13-dioate

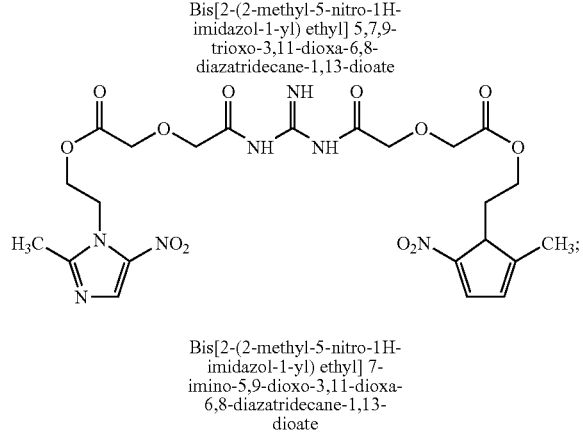

Bis[2-(2-methyl-5-nitro-1H-imidazol-1-yl) ethyl] 7-imino-5,9-dioxo-3,11-dioxa-6,8-diazatridecane-1,13-dioate or their pharmaceutical acceptable salts and/or hydrates, among other compounds.

The second objective of the present invention is the process for preparing the compounds of general formula (I) an (II). According to the present invention general compounds of formula (I) an (II) are prepared by reacting a urease affinity compound with the compound of general formula (III) represented below:

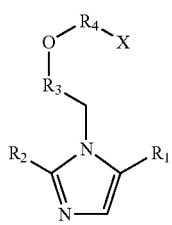

(III)

wherein $R_1$, $R_2$, $R_3$, $R_4$ are disclosed in general formula (I) represented above and X=OH or Cl. Compounds of general formula (II) are prepared by reacting the urease affinity compound with compounds of general formula (III) and (IV) represented below:

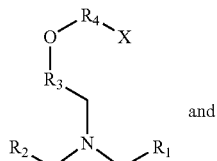

(III)

and

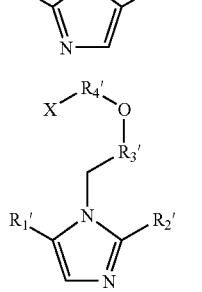

(IV)

wherein $R_1$, $R_1'$, $R_2$, $R_2'$, $R_3$, $R_3'$, $R_4$, $R_4'$ are disclosed in general formula (II) above described, and X=OH or Cl.

According to the process for preparing the compounds of general formula (I) and (II) of the present invention, when using intermediates of general formula (III) and/or (IV) above described wherein X=Cl, the reaction is performed directly with the urease affinity compound. Wherein X=OH, condensation agents, also known as coupling agents, are used.

Coupling agents preferably used in the process of the present invention are selected from the carbodiimide group, comprising preferably N,N'-dicyclohexyl carbodiimide (DCC), 1-ethyl-3-(3-dimethylaminopropyl) carbodiimide (EDC) and 1,3-diisopropyl carbodiimide (DCI).

According to the process for preparing the compounds of general formula (I) and (II), urease affinity compounds that are used are selected from the group comprising urea, N-hydroxyurea, N,N'-dihydroxyurea, bis-(hydroxymethil)urea, thiourea, N-hydroxythiourea, N,N'-dihydroxythiourea, bis-(hydroxymethyl)thiourea, guanidine, N-hydroxyguanidine, N,N'-dihydroxyguanidine and bis-(hydroxymethyl)guanidine.

General formula III and IV compounds preparing are well known in the art. In the case of the compounds of the present invention, they were prepared preferably through esterification of hydroxy-nitroimidazolic derivatives using the reaction with acid anhydrides with up to 14 carbon atoms in an alkaline medium.

Among hydroxyl-nitroimidazolic derivatives, preferably was used metronidazole (2-(2-methyl-5-nitro-1H-imidazol-1-yl)ethanol).

Among carboxylic acid anhydrides, preferably were used acid anhydrides selected from the group comprising succinic, glutaric and diglycolic anhydrides.

The alkaline pH was reached by using inorganic bases, such as sodium or potassium hydroxides. Preferably, sodium hydroxide was used as the alkaline agent.

For preparing compounds of general formula (I) the reaction takes place between the compound of formula (III) wherein X=OH or Cl, and the urease affinity compound in a ratio of 1:1. In the reaction medium, preferably the ratio between urease affinity compound and compound of formula (III) wherein X=OH or Cl can range from about 10:1 to 1:1 respectively, being preferably used a molar excess of the urease affinity compound, avoiding double condensation.

For preparing compounds of general formula (II) the reaction takes place between compounds of formula (III) and (IV) wherein X=OH or Cl and the urease affinity compound in a ratio of 2:1 respectively. In the reaction medium, preferably the ratio between the concentration of urease affinity compound and the concentration of compounds of formula (III) and (IV) wherein X=OH or Cl used can range from about 1:1 to 1:10 (urease affinity compound concentration and the sum of compounds of formula (III) and (IV) concentration respectively) depending on the reaction. There could exist special cases where the ratio between these reagents should be altered outside these limits, mainly because the solubility behavior of the compounds used in the reaction medium but, in general, these limits are efficient for preparing the disclosed compounds.

Another objective of the present invention are the pharmaceutical compositions comprising as the active ingredient a compound of general formula (I) or (II) and at least one pharmaceutical excipient selected from the acceptable pharmaceutical excipients used for preparing pharmaceutical compositions.

The compounds of the present invention can be prepared as several pharmaceutical compositions used for administering biological agents. The route of administration can be oral, topic, nasal, injectable, etc.

In the pharmaceutical composition of the present invention, the pharmaceutical active ingredient is selected from compounds of formula (I) or (II) and it is used in therapeutically acceptable concentrations ranging from 0.001% to 99.999% in weight of the final composition. In order to formulate dosage forms allowing appropriate way for its delivery, at least one pharmaceutical acceptable excipient is used providing suitable dilution for the active ingredient.

In a preferred embodiment of the present invention, the pharmaceutical composition comprises:

(a) a compound of formula (I) used in an amount of at least 0.001% in weight of the final composition, and (b) at least one pharmaceutical acceptable excipient.

In another preferred embodiment of the present invention the pharmaceutical composition comprises:

(c) a compound of formula (I) used in an amount of at least 1.0% in weight of the final composition, and (d) at least one pharmaceutical acceptable excipient.

For instance, the compound of the present invention can be formulated as powders or granules for oral administration by tablets, pills and hard gelatin capsules, where the formulation of the compounds can be enriched by the addition of several pharmaceutical excipients used to dilute the active ingredient, to facilitate compression and to confer several properties like immediate or controlled release, improved solubility and stability, among several other properties.

Compounds from the present invention can also be formulated as solutions suitable for oral administration like solutions, syrups, elixirs, or as solutions encapsulated in soft gelatin capsules. They can also be formulated as injectable solutions for being used in the aggressive treatment of several infections. They can also be formulated as pasts, creams, ointments, lotions or powders for topic administration.

Besides these possibilities, the compound of the present invention can be formulated with other auxiliary active pharmaceutical ingredients for the combined treatment of several infections, where the need for a multifunctional agent should be complemented by the action of other compounds for treating infections.

Consequently, the present invention also has as objective the use of active compound of general formula (I) and (II) in pharmaceutical compositions or formulations, or medicines for treating several infections in animals and/or humans and, in particular, for treating infections mediated by urease producing organisms like, for instance, *Helicobacter pylori*.

Another objective of the present invention is the method for treating individuals infected by *Helicobacter pylori*, which comprises administering an effective amount of the inventive compounds of general formula (I) or (II) as a pharmaceutical composition comprising one inventive compound and at least an acceptable pharmaceutical ingredient.

The following examples are illustrative but not exhaustive in describing the potentialities from the compound of the present invention as less mutagenic substances than their parent drugs, and their properties in inhibiting urease and their activity over microorganisms like, for example, *Helicobacter pylori*.

EXAMPLE 1

Synthesis of Metronidazole Monosuccinate

In a 100 mL reactor with 10 mL of methanol at a temperature about 60° C., add 0.315 g of metronidazole, 2.0 mL of NaOH 1N, 0.2 g of succinic anhydride and keep the reaction medium under stirring and heating for about 2 hours. Cool the reaction medium to a temperature around 8° C. and allow it to stand for 12 hours. The reaction medium is filtered and the solvent is evaporated to dryness yielding 0.47 g of metronidazole monosuccinate. (Yield=94%)

EXAMPLE 2

Synthesis of Metronidazole Monoglutarate

In a 100 mL reactor with 10 mL of methanol at a temperature about 60° C., add 0.300 g of metronidazole, 2.0 mL of NaOH 1N and keep under stirring for about 30 minutes. Add 0.2 g of glutaric anhydride and 11.0 mL of NaOH 1N and keep the reaction medium under stirring and heating for about 5 hours. Cool the reaction medium to a temperature around 8° C. and allow it to stand for 12 hours. The reaction medium is filtered and the solvent is evaporated to dryness yielding 0.30 g of metronidazole monoglutarate (Yield=60%). PF=203-205° C.

EXAMPLE 3

Synthesis of Metronidazole Monodiglycolate

In a 100 mL reactor with 10 mL of methanol at a temperature about 60° C., add 0.298 g of metronidazole, 3.0 mL of NaOH 1N, 0.252 g of diglycolic anhydride and keep the reaction medium under stirring and heating for about 5 hours. Cool the reaction medium to a temperature around 24° C. and keep it under stirring for 24 hours. Cool the reaction medium to a temperature around 8° C. and allow it to stand for 12 hours. The reaction medium is filtered and the solvent is evaporated to dryness yielding 0.20 g of metronidazole monodiglycolate. (Yield=40%). PF=139-145° C.

EXAMPLE 4

Synthesis of 2-(2-methyl-5-nitro-1H-imidazol-1-yl)ethyl 4-[(aminocarbonothioyl)amino]-4-oxobutanoate

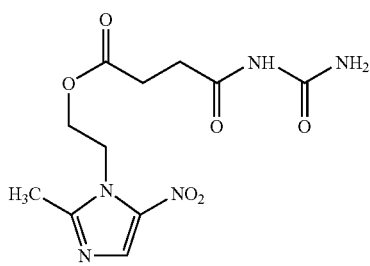

In a 100 mL reactor dissolve under stirring 0.27 g of metronidazole monosuccinate in 5 mL of N,N'-dimethylformamide. Cool the reaction medium to a temperature around 5° C. and add 0.36 mL of DCI (1,3-diisopropyl carbodiimide), 0.3 g of HOBT (1-hydroxybenzotriazole), adjust the pH in the range from about 8 to about 9 with TEA (triethylamine) and add 0.3 g of thiourea. Keep the reaction medium under stirring for about one hour, allow it to heat to the ambient temperature and keep it under stirring for about 23 hours. Add about 6 mL of NaHCO$_3$ 2.0M and extract the reaction medium with three 30 mL portions of ethyl acetate or diethyl ether. Wash the organic phase with an aqueous solution of citric acid 0.2M, separate the organic phase and dry with sodium sulfate. Filter the solid and evaporate the organic phase at a temperature of about 40° C. The crude product is crystallized from methanol yielding 78.42%. PF=106-108° C.

$^1$H NMR (DMSO-d6) δ 8.04 (s, 1H); 4.57 (t, 2H); 4.37 (t, 2H); 2.55 (t, 2H); 2.51 (t, 2H); 2.50 (s, 3H).

$^{13}$C NMR (DMSO-d6) δ 174.4; 171.3; 156.9; 132.0; 44.7; 42.3; 23.3; 22.4; 14.0.

IR (KBr): 3342, 3288, 1732, 1652, 1622, 1568, 1387, 1364, 1168, 1126, 1058.

EXAMPLE 5

Synthesis of Bis[2-(2-methyl-5-nitro-1H-imidazol-1-yl)ethyl]4,4'[(thioxomethylene)diimine]bis(4-oxobutanoate)

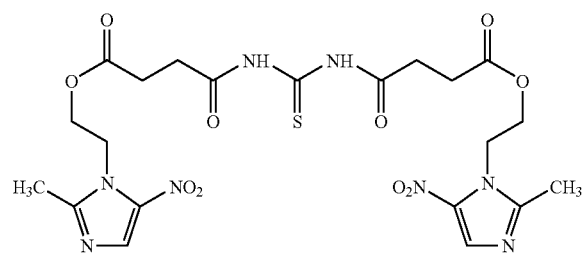

In a 100 mL reactor add 10 mL of THF (tetrahydrofuran) and heat to a temperature around 65° C. Under stirring dissolve 0.41 g of metronidazole monosuccinate, add slowly 0.13 mL of PCl$_3$ and wait for fumes dissipation. Adjust the pH to a range from 9 to 10 with triethylamine (around 0.5 mL) and add 0.12 g of thiourea. Keep the reaction medium under stirring for about 3 hours and evaporate THF to dryness. The product is purified by preparative chromatography in fluorescent silica plates of 50 micras width using methanol:chloroform as the mobile phase (70:20-volume:volume). Yield=0.45 g (90%).

$^1$H NMR (DMSO-d6) δ 8.00 (s, 2H); 4.38 (t, 4H); 3.68 (t, 4H); 2.56 (t, 4H); 2.52 (t, 4H); 2.47 (s, 6H);

$^{13}$C NMR (DMSO-d6) δ 183.9; 172.4; 171.3; 152.0; 132.9; 51.6; 48.3; 28.4; 13.1.

IR (KBr): 3303, 3193, 1731, 1656, 1616, 1533, 1396, 1365, 1170, 1058.

Mutagenic Activity Test

The mutagenic activity of the compounds were evaluated by The Ames Test without metabolic activation (–S9), with *Salmonella typhimurium* T-100 strain. The test is based in the fact that indicating *S. typhimurium* strains are sensitive to substances capable of inducing different kinds of mutation. In the presence of mutagenic agents, these strains revert the character of histidine auxotrophic synthesis, and start forming colonies in a medium were this aminoacid is absent. The mutagenic activity of a compound as its concentration function is established by counting the number of colonies per plate.

The final data obtained were analyzed by using Salanal software (*Salmonella* Assay Analysis) Version 1.0 from Research Triangle Institute, RTP, North Carolina, USA. This software allows to evaluate the dose-answer response by performing an analysis of variance (ANOVA f-test) between the mean revertants number in the different tested concentrations (doses) and the negative control, followed by a linear regression. For the data analysis it was selected the Bernstein Method (Bernstein et al, 1982). The slope of the linear part of response-dosage curve is also furnished by the program and it corresponds to the number of revertants induced per mg of the sample analyzed.

From these data, mutagenicity ratio (MR) was calculated for each concentration (dose) analyzed for each compound.

MR is calculated by the following equation:

$$MR = \frac{\text{mean of revertants per tested plates (spontaneous + induced)}}{\text{mean of revertants per negative control plates (spontaneous)}}$$

wherein spontaneous means the revertant number developed in a plate, independent for being induced or not, considering as positive response values ≧2 (Valent et al, 1993).

Mutagenic activity obtained for the compounds of the present invention are disclosed in table 1. Listed values correspond to the mean±the standard deviation of the revertant colonies per plate and the correspondent calculated mutagenic rate (MR).

TABLE 1

Mutagenic activity and mutagenic rate as a function of concentration of the tested drug

| Concentration (mM)/plate | Metronidazole | Example 1 | Example 4 | Example 5 |
|---|---|---|---|---|
| 0 | 123 ± 13 | 106 ± 8 | 86 ± 2 | 126 ± 3 |
| 2.9 | 376 ± 38 | 175 ± 37 | 92 ± 2 | 162 ± 29 |
|  | RM = 3.1 | RM = 1.6 | RM = 1.1 | RM = 1.3 |

TABLE 1-continued

Mutagenic activity and mutagenic rate as a function of concentration of the tested drug

| Concentration (mM)/plate | Metronidazole | Example 1 | Example 4 | Example 5 |
|---|---|---|---|---|
| 14.6 | 1059 ± 103 | 420 ± 90 | 166 ± 32 | 316 ± 19 |
|  | RM = 8.6 | RM = 4.0 | RM = 1.9 | RM = 2.5 |
| 29.2 | 1626 ± 77 | 954 ± 101 | 225 ± 14 | 606 ± 94 |
|  | RM = 13.2 | RM = 9.0 | RM = 2.6 | RM = 4.8 |
| 58.4 | 1832 ± 36 | 1674 ± 233 | 371 ± 61 | 1095 ± 100 |
|  | RM = 14.9 | RM = 15.8 | RM = 4.3 | RM = 8.7 |
| 116.9 | 1053 ± 227 | 1181 ± 224 | 708 ± 35 | 1582 ± 79 |
|  | RM = 8.6 | RM = 11.1 | RM = 8.2 | RM = 12.5 |

With the results from table 1 there was plotted the graphic from FIG. 1, where it is possible to observe that the inventive compounds from examples 4 and 5 presents a mutagenic activity very inferior than the mutagenic activity for metronidazole parent drug or its monosuccinate ester derivative (example 1). From the graphic from FIG. 1 it is also possible to notice that in concentrations above 58.4 mM/plate, metronidazole and metronidazole monosuccinate are toxic and kill the cells used in the assay. This effect can be observed by the falling of the corresponding slopes plotted for metronidazole and the compound from example 1.

Activity Test Against *Helicobacter Pylori*

The present invention compounds were evaluated for their activity against *Helicobacter pylori* by using the method described by Magãlhaes, P. P. et al—*Helicobacter pylori* Primary Resistance to Metronidazole and Clarithromycin in Brazil—Antimicrobial Agents and Chemotherapy, Vol. 46, No. 6, p. 2021-2023 June 2002, and the results are disclosed in table 2.

TABLE 2

Helicobacter pylori Evaluation Activity

| COMPOUND | Culture 627-99 Concentration (μmol/plate) | | | Culture 712-00 Concentration (μmol/plate) | | |
|---|---|---|---|---|---|---|
|  | 0.0234 | 0.0467 | 0.0935 | 0.0234 | 0.0467 | 0.0935 |
| Metronidazole | + | + | + | + | + | + |
| Example 1 | + | + | + | + | + | + |
| Example 4 | + | + | + | + | + | + |
| Example 5 | + | + | + | + | + | + |

In this experiment there were tested metronidazole (MDZ), metronidazole monosuccinate (example 1) and the inventive compounds from examples 4 and 5. Two cultures from different origins were used.

The activity test against *Helicobacter pylori*, shows that the inventive compounds are active since the minimum inhibition concentration (MIC) used for the evaluation of metronidazole, demonstrating that they posses at least the same activity of the parent drug against *H. pylori*.

Urease Inhibiting Test

Urease inhibition is evaluated by the assay based on RUÍZ-HERRERA, J; GONZALEZ, L. A (1969) and has the objective to verify in the visible spectra, by using phenol red as indicator, the formation of ammonium from urea according to the following reaction:

$$CO(NH_2)_2 + 2H_2O + H^+ \xrightarrow{UREASE} 2NH_4^+ + HCO_3^-$$

According to the test, as less ammonium is formed, the higher is the activity of the compound tested in inhibiting urease.

Metronidazole and the inventive compounds from examples 4 and 5 were submitted to this assay by using a concentration of 30 mM for each compound. The inhibiting percentage for each compound is presented in table 3.

TABLE 3

Urease inhibiting percentage for metronidazole, thiourea, compound from example 4 and from example 5 in a molar concentration of 30 nM

| | Inhibiting percentage/time | | |
|---|---|---|---|
| | 1 minute | 2 minutes | 3 minutes |
| Metronidazole | 6 | 7 | 7 |
| Tiourea | 23 | 16 | 17 |
| Example 4 | 96 | 98 | 98 |
| Example 5 | 74 | 67 | 65 |

Figure 2:
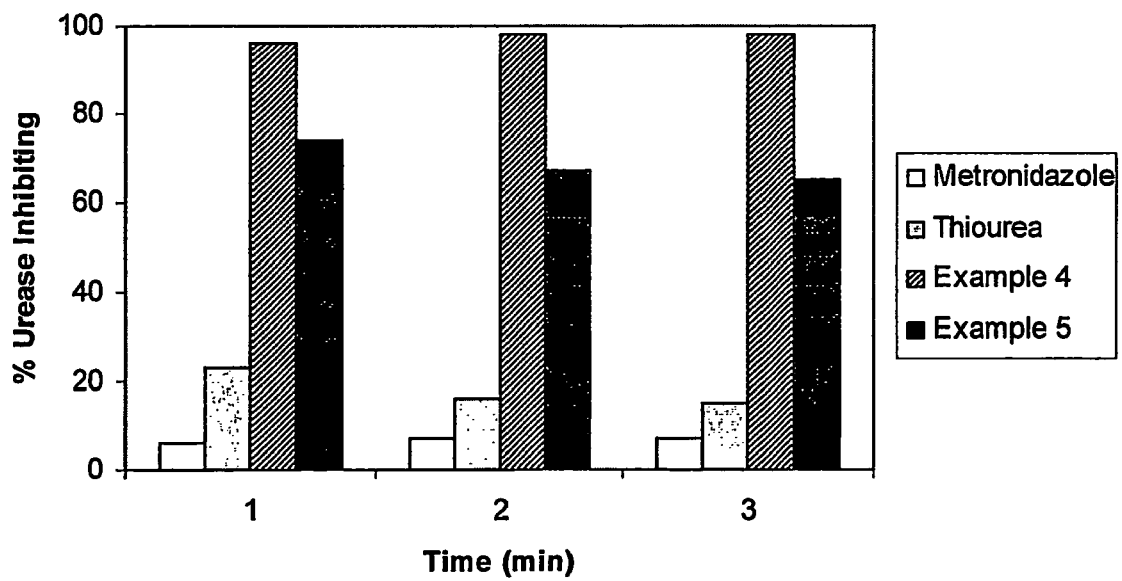

These results can be better visualized by the graphic from FIG. 2, where it is possible to observe the markedly urease inhibiting percentage presented by the compounds of the present invention.

The results from the tests disclosed above demonstrate the importance of the compounds of the present invention, which posses a reduced mutagenic profile, are potent urease inhibitors that they are at least as active as the parent drug they derived from.

The invention claimed is:

1. A compound represented by the formula (I)

$$\text{(I)}$$

[structure of formula (I) showing imidazole ring with substituents $R_1$, $R_2$, $R_3$, and $O-R_4-R_5$ group]

or its pharmaceutically acceptable salts, wherein:
$R_1$=NO$_2$, $R_2$=CH$_3$ and $R_3$=CH$_2$, CHCH$_3$, CHCH$_2$Cl OR
$R_1$=H, $R_2$=NO$_2$ and $R_3$=O(CH$_2$)$_4$, OCH$_2$(CH$_2$CH$_2$, OCH$_2$—C≡C—CH$_2$, CHCH$_2$OCH$_3$, CONH(CH$_2$)$_{1-2}$,

[structure: CH—CH$_2$—N with cyclopropyl], and $R_4$ = $-\overset{O}{\underset{\|}{C}}-$ , $-\overset{O}{\underset{\|}{C}}-CH_2(CH_2)_n-\overset{O}{\underset{\|}{C}}-$ , $-\overset{O}{\underset{\|}{C}}-CH_2O(CH_2)_n-\overset{O}{\underset{\|}{C}}-$ , CH$_2$CO, wherein n=1-6
$R_5$=NHCONH$_2$, NHCONHOH, ONHCONHOH, OCH$_2$NHCONHCH$_2$OH, NHCSNH$_2$, NHCSNHOH, ONHCSNHOH, OCH$_2$NHCSNHCH$_2$OH, NHCNHNH$_2$, NHCNHNHOH, ONHCNHNHOH, OCH$_2$NHCNHNHCH$_2$OH.

2. The compound according to claim 1, wherein $R_1$=NO$_2$, $R_2$=CH$_3$,

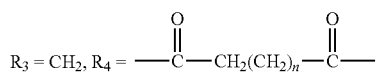

wherein n=1, and $R_5$=NHCSNH$_2$.

3. A process for preparing a compound of the formula (I)

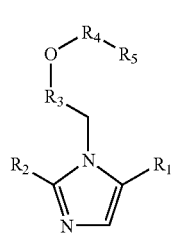

wherein:
$R_1$=NO$_2$, $R_2$=CH$_3$ and $R_3$=CH$_2$, CHCH$_3$, CHCH$_2$Cl
OR
$R_1$=H, $R_2$=NO$_2$ and $R_3$=O(CH$_2$)$_4$, OCH$_2$(CH)$_2$CH$_2$, OCH$_2$—C≡C—CH$_2$, CHCH$_2$OCH$_3$, CONH(CH$_2$)$_{1-2}$,

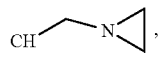

and

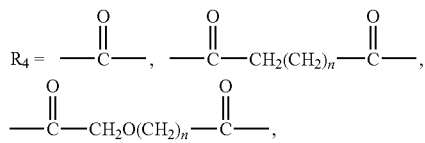

CH$_2$CO, wherein n=1-6
$R_5$=NHCONH$_2$, NHCONHOH, ONHCONHOH, OCH$_2$NHCONHCH$_2$OH, NHCSNH$_2$, NHCSNHOH, ONHCSNHOH, OCH$_2$NHCSNHCH$_2$OH, NHCNHNH$_2$, NHCNHNHOH, ONHCNHNHOH, OCH$_2$NHCNHNHCH$_2$OH
which comprises reacting a compound of formula (III)

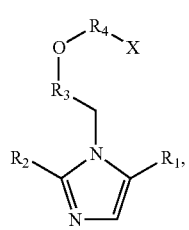

wherein $R_1$, $R_2$, $R_3$, $R_4$ are described above and X=OH or Cl, with an urease affinity compound selected from the group consisting of urea, N-hydroxyurea, N,N'-dihydroxyurea, bis-(hydroxymethil)urea, thiourea, N-hydroxythiourea, N,N'-dihydroxythiourea, bis-(hydroxymethyl)thiourea, guanidine, N-hydroxyguanidine, N,N'-dihydroxyguanidine and bis-(hydroxymethyl)guanidine.

4. The process according to claim 3, wherein for X=OH the reaction with the urease affinity compound is done by using a coupling agent selected from the group consisting of N,N'-dicyclohexyl carbodiimide (DCC), 1-ethyl-3-(3-dimethylaminopropyl) carbodiimide (EDC) and 1,3-diisopropyl carbodiimide (DCI).

5. A pharmaceutical composition comprising:
a) a compound of claim 1 in an amount of at least 0.001% in weight of the final composition, and
b) at least one pharmaceutically acceptable excipient.

6. A compound selected from the group consisting of:
2-(2-methyl-5-nitro-1H-imidazol-1-yl)ethyl 4-[(aminocarbonothioyl)amino]-4-oxobutanoate;
2-(2-methyl-5-nitro-1H-imidazol-1-yl)ethyl 4-[(aminocarbonyl)amino]-4-oxobutanoate;
2-(2-methyl-5-nitro-1H-imidazol-1-yl)ethyl 4-{[amino(imino)methyl]amino}-4-oxobutanoate;
2-(2-methyl-5-nitro-1H-imidazol-1-yl)ethyl 4-{[(hydroxyamino)carbonothioyl]amino}-4-oxobutanoate;
2-(2-methyl-5-nitro-1H-imidazol-1-yl)ethyl 4-{[(hydroxyamino)carbonyl]amino}-4-oxobutanoate;
2-(2-methyl-5-nitro-1H-imidazol-1-yl)ethyl 4-{[(hydroxyamino)(imino)methyl]amino}-4-oxobutanoate;
2-(2-methyl-5-nitro-1H-imidazol-1-yl)ethyl 5-[(aminocarbonothioyl)amino]-5-oxopentanoate;
2-(2-methyl-5-nitro-1H-imidazol-1-yl)ethyl 5-[(aminocarbonyl)amino]-5-oxopentanoate;
2-(2-methyl-5-nitro-1H-imidazol-1-yl)ethyl 5-{[amino(imino)methyl]amino}-5-oxopentanoate;
2-(2-methyl-5-nitro-1H-imidazol-1-yl)ethyl 5-{[(hydroxyamino)carbonothioyl]amino}-5-oxopentanoate;
2-(2-methyl-5-nitro-1H-imidazol-1-yl)ethyl 5-{[(hydroxyamino)carbonyl]amino}-5-oxopentanoate;
2-(2-methyl-5-nitro-1H-imidazol-1-yl)ethyl 5-{[(hydroxyamino)(imino)methyl]amino}-5-oxopentanoate;
2-(2-methyl-5-nitro-1H-imidazol-1-yl)ethyl {2-[(aminocarbonothioyl)amino]-2-oxoethoxy}acetate;
2-(2-methyl-5-nitro-1H-imidazol-1-yl)ethyl {2-[(aminocarbonyl)amino]-2-oxoethoxy}acetate;
2-(2-methyl-5-nitro-1H-imidazol-1-yl)ethyl (2-{[amino(imino)methyl]amino}-2-oxoethoxy)acetate;
2-(2-methyl-5-nitro-1H-imidazol-1-yl)ethyl (2-{[(hydroxyamino)carbonothioyl]amino}-2-oxoethoxy)acetate;
2-(2-methyl-5-nitro-1H-imidazol-1-yl)ethyl (2-{[(hydroxyamino)carbonyl]amino}-2-oxoethoxy)acetate; and
2-(2-methyl-5-nitro-1H-imidazol-1-yl)ethyl (2-{[(hydroxyamino)(imino)methyl]amino}-2-oxoethoxy)acetate;
or their pharmaceutically acceptable salts.

7. A pharmaceutical composition comprising as pharmaceutical active ingredient a compound according with claim 6, which is used in an amount of at least 0.001% in weight of the final composition, and at least a pharmaceutically acceptable ingredient.

8. A method for treating a bacterial or parasitic infection comprising administering to a subject infected by a bacterium or parasite an effective amount of a pharmaceutical composition comprising a compound of the formula (I)

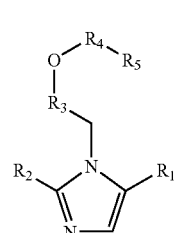

wherein:
$R_1$=NO$_2$, $R_2$=CH$_3$ and $R_3$=CH$_2$, CHCH$_3$, CHCH$_2$Cl
OR

R₁=H, R₂=NO₂ and R₃=O(CH₂)₄, OCH₂(CH)₂CH₂, OCH₂—C=C—CH₂, CHCH₂OCH₃, CONH(CH₂)₁₋₂,

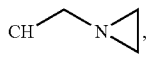

and

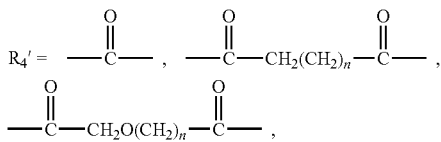

CH₂CO, wherein n=1-6
R₅=NHCONH₂, NHCONHOH, ONHCONHOH, OCH₂NHCONHCH₂OH, NHCSNH₂, NHCSNHOH, ONHCSNHOH, OCH₂NHCSNHCH₂OH, NHCNHNH₂, NHCNHNHOH, ONHCNHNHOH, OCH₂NHCNHNHCH₂OH.

9. The method according to claim 8, wherein in the compound of formula (I),

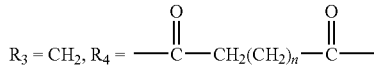

wherein n=1, and R₅=NHCSNH₂.

10. The method according to claim 8, wherein the compound according to formula (I) is selected from the group consisting of:

2-(2-methyl-5-nitro-1H-imidazol-1-yl)ethyl 4-[(aminocarbonothioyl)amino]-4-oxobutanoate;
2-(2-methyl-5-nitro-1H-imidazol-1-yl)ethyl 4-[(aminocarbonyl)amino]-4-oxobutanoate;
2-(2-methyl-5-nitro-1H-imidazol-1-yl)ethyl 4-{[amino(imino)methyl]amino}-4-oxobutanoate;
2-(2-methyl-5-nitro-1H-imidazol-1-yl)ethyl 4-{[(hydroxyamino)carbonothioyl]amino}-4-oxobutanoate;
2-(2-methyl-5-nitro-1H-imidazol-1-yl)ethyl 4-{[(hydroxyamino)carbonyl]amino}-4-oxobutanoate;
2-(2-methyl-5-nitro-1H-imidazol-1-yl)ethyl 4-{[(hydroxyamino)(imino)methyl]amino}-4-oxobutanoate;
2-(2-methyl-5-nitro-1H-imidazol-1-yl)ethyl 5-[(aminocarbonothioyl)amino]-5-oxopentanoate;
2-(2-methyl-5-nitro-1H-imidazol-1-yl)ethyl 5-[(aminocarbonyl)amino]-5-oxopentanoate;
2-(2-methyl-5-nitro-1H-imidazol-1-yl)ethyl 5-{[amino(imino)methyl]amino}-5-oxopentanoate;
2-(2-methyl-5-nitro-1H-imidazol-1-yl)ethyl 5-{[(hydroxyamino)carbonothioyl]amino}-5-oxopentanoate;
2-(2-methyl-5-nitro-1H-imidazol-1-yl)ethyl 5-{[(hydroxyamino)carbonyl]amino}-5-oxopentanoate;
2-(2-methyl-5-nitro-1H-imidazol-1-yl)ethyl 5-{[(hydroxyamino)(imino)methyl]amino}-5-oxopentanoate;
2-(2-methyl-5-nitro-1H-imidazol-1-yl)ethyl {2-[(aminocarbonothioyl)amino]-2-oxoethoxy}acetate;
2-(2-methyl-5-nitro-1H-imidazol-1-yl)ethyl {2-[(aminocarbonyl)amino]-2-oxoethoxy}acetate;
2-(2-methyl-5-nitro-1H-imidazol-1-yl)ethyl (2-{[amino(imino)methyl]amino}-2-oxoethoxy)acetate;
2-(2-methyl-5-nitro-1H-imidazol-1-yl)ethyl (2-{[(hydroxyamino)carbonothioyl]amino}-2-oxoethoxy)acetate;
2-(2-methyl-5-nitro-1H-imidazol-1-yl)ethyl (2-{[(hydroxyamino)carbonyl]amino}-2-oxoethoxy)acetate; and
2-(2-methyl-5-nitro-1H-imidazol-1-yl)ethyl (2-{[(hydroxyamino)(imino)methyl]amino}-2-oxoethoxy)acetate.

11. The compound of claim 1 that inhibits a urease enzyme.

* * * * *